United States Patent
Shim et al.

(10) Patent No.: US 9,511,172 B2
(45) Date of Patent: Dec. 6, 2016

(54) METHOD FOR MANUFACTURING ALLOGENEIC SOFT-TISSUE TRANSPLANT HAVING AUTOLOGOUS STEM CELL TRANSPLANTED THEREIN

(75) Inventors: Young Bock Shim, Seoul (KR); Kwang Il Lee, Anyang-si (KR); Ju Woong Jang, Seoul (KR); Jung Soo Lee, Suwon-si (KR)

(73) Assignee: Cellumed Co., Ltd., Seoul (KR)

( * ) Notice: Subject to any disclaimer, the term of this patent is extended or adjusted under 35 U.S.C. 154(b) by 339 days.

(21) Appl. No.: 14/002,104

(22) PCT Filed: Feb. 24, 2012

(86) PCT No.: PCT/KR2012/001443
§ 371 (c)(1),
(2), (4) Date: May 30, 2014

(87) PCT Pub. No.: WO2012/118305
PCT Pub. Date: Sep. 7, 2012

(65) Prior Publication Data
US 2015/0209476 A1    Jul. 30, 2015

(30) Foreign Application Priority Data

Feb. 28, 2011  (KR) .................. 10-2011-0018216
Feb. 23, 2012  (KR) .................. 10-2012-0018650

(51) Int. Cl.
| | | |
|---|---|---|
| *C12N 5/00* | (2006.01) | |
| *A61L 27/36* | (2006.01) | |
| *A61L 27/56* | (2006.01) | |
| *A61L 27/38* | (2006.01) | |

(52) U.S. Cl.
CPC ........ *A61L 27/3687* (2013.01); *A61L 27/3604* (2013.01); *A61L 27/3691* (2013.01); *A61L 27/3834* (2013.01); *A61L 27/56* (2013.01); *A61L 2300/64* (2013.01); *A61L 2430/34* (2013.01)

(58) Field of Classification Search
None
See application file for complete search history.

(56) References Cited

U.S. PATENT DOCUMENTS

| 6,908,591 B2 | 6/2005 | MacPhee et al. |
| 7,754,232 B2 * | 7/2010 | Fisher .................. A61L 27/3691 424/423 |

FOREIGN PATENT DOCUMENTS

| KR | 10-0365573 | 8/2004 |
| KR | 10-0839875 | 6/2008 |
| KR | 10-0920951 | 10/2009 |
| KR | 10-2010-0005105 | 1/2010 |
| WO | 95/24873 | 9/1995 |
| WO | 2008/146956 | 12/2008 |

OTHER PUBLICATIONS

Gilbert et al., Biomaterials, 2006, vol. 27, p. 3675-3683.*
Joshi et al., J. Ortho. Res., 2008, vol. 26, p. 1105-1113.*
Altman et al., The FASEB Journal express article 10.1096/fj.01-0656fje. Published online Dec. 28, 2001, 13 pages of PDF.*
International Search Report and Written Opinion of the International Search Authority from PCT/KR2012/001443, dated Sep. 28, 2012, (6 pgs.).

* cited by examiner

*Primary Examiner* — Kade Ariani
(74) *Attorney, Agent, or Firm* — Nixon Peabody LLP; Khaled Shami

(57) ABSTRACT

Provided is a method of manufacturing an allogeneic soft-tissue transplant having autologous stem cells transplanted therein using an allogeneic soft-tissue support that is obtained from an allogeneic organism. In this regard, an allogeneic soft-tissue transplant that can replace a damaged soft-tissue of a human body is manufactured.

15 Claims, 12 Drawing Sheets

SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: Forward primer sequences of Collagen I gene

<400> SEQUENCE: 1
cagggtgttc ctggagacct                                           20

<210> SEQ ID NO 2
<211> LENGTH: 20
<212> TYPE: DNA
<213> ORGANISM: Artificial
<220> FEATURE:
<223> OTHER INFORMATION: Reverse primer sequences of Collagen I gene

<400> SEQUENCE: 2
aggagagcca tcagcacctt                                           20

<210> SEQ ID NO 3
<211> LENGTH: 20
<212> TYPE: DNA
<213> ORGANISM: Artificial
<220> FEATURE:
<223> OTHER INFORMATION: Forward primer sequences of Collagen III gene

<400> SEQUENCE: 3
gaaaatggaa aacctgggga                                           20

<210> SEQ ID NO 4
<211> LENGTH: 20
<212> TYPE: DNA
<213> ORGANISM: Artificial
<220> FEATURE:
<223> OTHER INFORMATION: Reverse primer sequences of Collagen III gene

<400> SEQUENCE: 4
caccctttgg accaggactt                                           20

<210> SEQ ID NO 5
<211> LENGTH: 20
<212> TYPE: DNA
<213> ORGANISM: Artificial
<220> FEATURE:
<223> OTHER INFORMATION: Forward primer sequences of Tenascin-C gene

<400> SEQUENCE: 5
tacagcctgg cagacctgag                                           20

<210> SEQ ID NO 6

```
<211> LENGTH: 20
<212> TYPE: DNA
<213> ORGANISM: Artificial
<220> FEATURE:
<223> OTHER INFORMATION: Reverse primer sequences of Tenascin-C gene

<400> SEQUENCE: 6
attgcttggg agcagtcctt                                              20

<210> SEQ ID NO 7
<211> LENGTH: 20
<212> TYPE: DNA
<213> ORGANISM: Artificial
<220> FEATURE:
<223> OTHER INFORMATION: Forward primer sequences of GAPDH gene

<400> SEQUENCE: 7
aagggtcatc atctctgccc                                              20

<210> SEQ ID NO 8
<211> LENGTH: 20
<212> TYPE: DNA
<213> ORGANISM: Artificial
<220> FEATURE:
<223> OTHER INFORMATION: Reverse primer sequences of GAPDH gene

<400> SEQUENCE: 8
gtgatggcat ggactgtggt                                              20
```

METHOD FOR MANUFACTURING ALLOGENEIC SOFT-TISSUE TRANSPLANT HAVING AUTOLOGOUS STEM CELL TRANSPLANTED THEREIN

CROSS REFERENCE TO RELATED PATENT APPLICATION

This application is a national stage application under 35 U.S.C. 371 from PCT Application No. PCT/KR2012/001443, filed Feb. 24, 2012, which claims the benefit of Korean Patent Application Nos. 10-2011-0018216, filed on Feb. 28, 2011 and 10-2012-0018650, filed on Feb. 23, 2012, in the Korean Intellectual Property Office, the disclosure of which is incorporated herein in its entirety by reference.

TECHNICAL FIELD

The present disclosure relates to a method for manufacturing an allogeneic soft-tissue transplant transplanted in a human body using an allogeneic soft-tissue support that is derived from an allogeneic organism.

BACKGROUND ART

Globally, people are becoming more health conscious in the modern era. In particular, regular exercise has become recognized as an essential condition for maintaining a healthy life. An appropriate level of exercise is helpful for maintaining health, but an immoderate level of exercise can actually be harmful to health. As a representative example, in the case of a patient's musculoskeletal system being damaged due to an immoderate level of exercise, the patient may barely be able to move and frequently recovery is difficult unless physical therapies and other treatments are provided for a long period of time. In particular, damage to the cruciate ligament in the knee joint cannot be healed solely from physical therapy, and transplanting autologous tissues of the patient is a recognized treatment strategy. However, the transplant of autologous tissue also requires consistent rehabilitation treatment, and the transplanted autologous tissue lacks physical properties of the original ligament and hence cannot be considered as a practical treatment. Therefore, an allogeneic soft-tissue transplant, which maintains unique physical properties, reduces immunological rejection significantly and replaces the patient's original soft-tissue as similarly as possible, is necessary to cure damaged ligaments, which are damaged soft-tissues.

DETAILED DESCRIPTION OF THE INVENTION TECHNICAL PROBLEM

Technical Problem

An embodiment of the present invention provides a method of manufacturing an allogeneic soft-tissue transplant having autologous stem cells transplanted therein using an allogeneic soft-tissue support that is derived from an allogeneic organism, to efficiently replace a damaged soft-tissue of a human body.

Technical Solution

According to an aspect of the present invention, there is provided a method of manufacturing an allogeneic soft-tissue transplant having autologous stem cells transplanted therein, the method including: obtaining an allogeneic soft-tissue support from a body of a human or an animal; washing and sterilizing the obtained allogeneic soft-tissue support; removing immunological rejection cells by treating the washed and sterilized allogeneic soft-tissue support with an enzyme solution; forming at least one pore in the allogeneic soft-tissue support in which the immunological rejection cells are removed; injecting autologous stem cells of a user into the pores; and incubating the allogeneic soft-tissue support in which the autologous stem cells are injected.

According to an embodiment of the present invention, the allogeneic soft-tissue support may be a ligament connected to a bone fragment.

According to another embodiment of the present invention, the washing and sterilizing may include treating the obtained allogeneic soft-tissue support with hydrogen peroxide and applying ultrasonic waves to the obtained allogeneic soft-tissue support.

According to another embodiment of the present invention, the hydrogen peroxide may have a concentration in a range from about 0.1 to about 5.0% and the ultrasonic waves may have an output in a range from about 120 to 400 watt (W).

According to another embodiment of the present invention, the washing and sterilizing may include treating the obtained allogeneic soft-tissue support with a radioprotectant and irradiating the allogeneic soft-tissue support.

According to another embodiment of the present invention, the radioprotectant is cobalt-60 ($Co^{60}$) and the irradiation is gamma ray irradiation in a range from about 12 to about 50 kilogray (kGy).

According to another embodiment of the present invention, the removing the immunological rejection cells may include treating the allogeneic soft-tissue support with an enzyme solution containing trypsin, collagenase, and protease.

According to another embodiment of the present invention, the removing the immunological rejection cells may further include water washing the sterilized allogeneic soft-tissue support with physiological saline after being treated with the enzyme solution.

According to another embodiment of the present invention, the removing the immunological rejection cells may further include washing with distilled water by osmotic treatment after the water washing of the allogeneic soft-tissue support with the physiological saline after being treated with the enzyme solution.

According to another embodiment of the present invention, the forming at least one pore may include a pore having a size in a range from about 1 to about 1,000 micrometer (µm) range.

According to another embodiment of the present invention, the injecting the autologous stem cells may further include injecting a supported catalyst for the autologous stem cells before or at a time of injecting the autologous stem cells.

According to another embodiment of the present invention, the incubating the allogeneic soft-tissue support may further include providing a physical stimulus to the allogeneic soft-tissue support.

According to another embodiment of the present invention, the physical stimulus may occur at a frequency of less than 1 Hz.

According to another embodiment of the present invention, the providing a physical stimulus includes providing tensile stress to two opposite distal ends of the allogeneic soft-tissue support, providing torsion to the allogeneic soft-tissue support in two opposite horizontal directions with respect to a vertical axis of the allogeneic soft-tissue support, or providing both tensile stress tensile stress to two opposite distal ends of the allogeneic soft-tissue support and torsion to the allogeneic soft-tissue support in two opposite horizontal directions with respect to a vertical axis of the allogeneic soft-tissue support, at the same time.

According to another embodiment of the present invention, the providing of tensile stress to two opposite distal ends of the allogeneic soft-tissue support may include extending the two opposite distal ends of the allogeneic soft-tissue support longitudinally, wherein one distal end is extended in a range from 0 to about 10% based on a total length of the allogeneic soft-tissue support and the other distal end is extended in a range from 0 to about 10% based on a total length of the allogeneic soft-tissue support, at the same time.

According to another embodiment of the present invention, the providing torsion to the allogeneic soft-tissue support in two opposite horizontal directions along a vertical axis of the allogeneic soft-tissue support may include rotating the two distal ends of the allogeneic soft-tissue support, wherein one distal end is rotated in a range from 0 to about 45 degrees clockwise and the other distal end is rotated in a range from 0 to 45 degrees counterclockwise, at the same time.

According to another embodiment of the present invention, the incubating may be performed for less than 7 days.

Advantageous Effects

According to a method of manufacturing an allogeneic soft-tissue transplant of the present invention, an allogeneic soft-tissue transplant that can efficiently replace a damaged soft-tissue of a human body may be manufactured by injecting an allogeneic soft-tissue support obtained from an allogeneic organism and by incubating the allogeneic soft-tissue support.

BEST MODE

An embodiment of the present invention will now be described in detail with reference to the accompanying drawings. The explanations hereafter are provided merely for comprehension of some embodiments of the present invention and are not intended to limit the scope of the invention.

Figure 1:
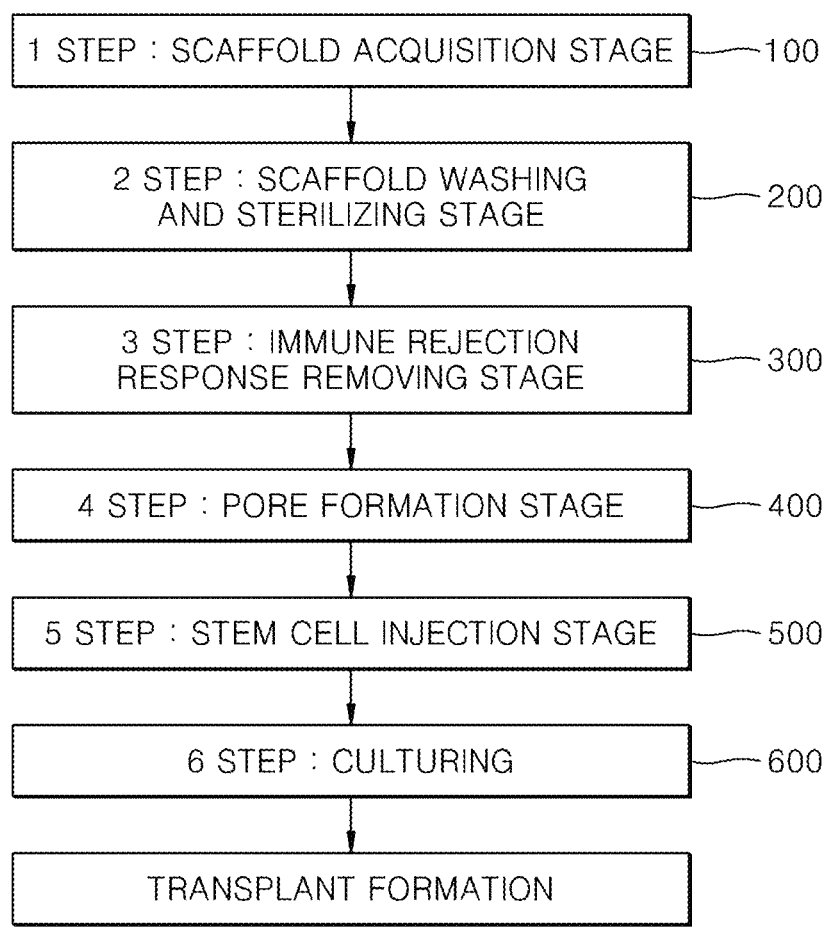
FIG. 1 is a flowchart of a method of manufacturing an allogeneic soft-tissue transplant according to an embodiment of the present invention.

FIG. 1 is a flowchart of a method of manufacturing an allogeneic soft-tissue transplant according to an embodiment of the present invention.

The method of manufacturing the allogeneic soft-tissue transplant includes obtaining an allogeneic soft-tissue support from a body of a human or an animal (step 100); washing and sterilizing the obtained allogeneic soft-tissue support (step 200); removing immunological rejection cells by treating the washed and sterilized allogeneic soft-tissue support with an enzyme solution (step 300); forming at least one pore in the allogeneic soft-tissue support in which the immunological rejection cells are removed (step 400); injecting autologous stem cells of a user into the pores (step 500); and incubating the allogeneic soft-tissue support in which the autologous stem cells are injected (step 600).

Referring to FIG. 1, the method of manufacturing the allogeneic soft-tissue transplant includes obtaining the allogeneic soft-tissue support from a body of a human or an animal (step 100). The soft-tissue refers to a non-bone tissue inside a body that connects, supports or surrounds organs or other structures of the body, and examples thereof are a ligament, a tendon, an Achilles' tendon and a tibialis tendon. The soft-tissue may be distributed in sections that support or maintain bodyweight and may serve to support and maintain repetitive movements, such as bending, twisting, and rotation. The soft-tissue may be particularly related with movement of the body, and thus may critically hinder kinetic functions when the soft-tissue or a section of a body related to the tissue is damaged. Meanwhile, the term "allogeneic" used herein refers to a group of organisms that are alike or to a relationship that may be medically recognized as the same type of organism. Therefore, an allogeneic soft-tissue transplant according to the present invention is a transplant including a soft-tissue that may be mutually transplanted in the same organism or between medically recognized allogeneic organisms. The allogeneic soft-tissue support refers to a support replaced to a treatment section as a body structure that has been separated directly from the recipient or from a medically recognized allogeneic organism. Additionally, the allogeneic soft-tissue support may be legally collected from a donated corpse. The allogeneic soft-tissue support may be a structure separated from a body, but it may also be combined with other body structures for an appropriate implant. For example, the allogeneic soft-tissue support may be a ligament, but may also be a structure connected to a bone fragment, for example a bone-ligament complex structure or a bone-ligament-bone complex structure. In addition, the allogeneic soft-tissue support may be transplanted to have different sizes and/or shapes according to the transplanted body section.

Referring to FIG. 1, the method of manufacturing the allogeneic soft-tissue transplant includes washing and sterilizing the obtained allogeneic soft-tissue support (step 200). In order for the allogeneic soft-tissue transplant to be transplanted into another body without any side effects or complications, not only foreign substances of the allogeneic soft-tissue support from a body of a human or an animal, but harmful bacteria also must be completely removed as much as possible. The washing and sterilizing (step 200) may be performed by using various physical or chemical methods, but both physical and chemical methods may be used at the same time. The washing and sterilizing (step 200) may be performed by using various methods to wash and sterilize the obtained allogeneic soft-tissue support physically and/or chemically, and a detailed explanation thereof will be given with respect to FIG. 2.

Referring to FIG. 1, the method of manufacturing the allogeneic soft-tissue transplant includes removing immunological rejection cells by treating the washed and sterilized allogeneic soft-tissue support with an enzyme solution (step 300). The enzyme solution is used to remove original cells existing in a body of a human or an animal before transplanting the transplant that has obtained the allogeneic soft-tissue support. The original cells existing in the body of the human or animal before the transplant may serve as antigens in an immune system of a body of another human or animal. Various immune responses are induced in the transplanted body in cases, and an unexpected side effect may occur from muscular pain or twitching in the process of such an immunological response. Therefore, it is necessary to inhibit the immune rejection responses by administering treatment by using various enzymes that may remove the original cells included in the allogeneic soft-tissue transplant. Removing the immunological rejection cell by treating the allogeneic soft-tissue support with an enzyme solution may be performed by using various methods, and a detailed description thereof will be provided with respect to FIG. 3 below.

Figure 4:
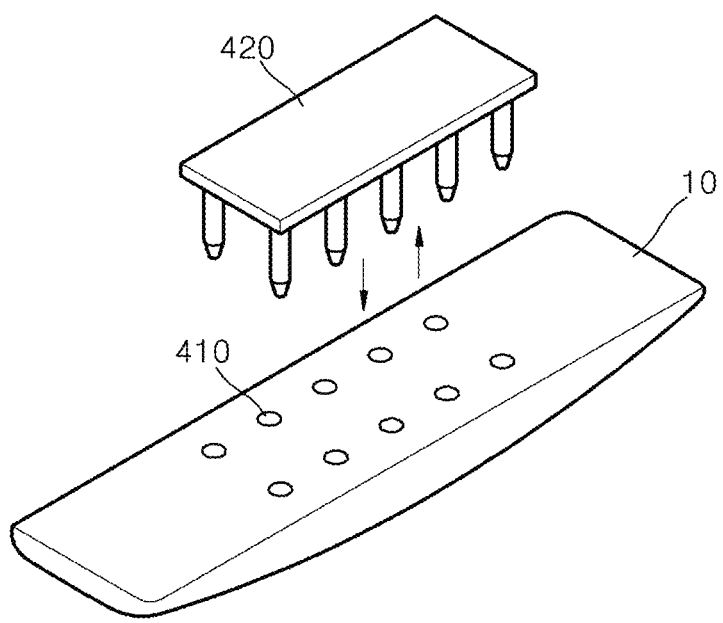
FIG. 4 is a diagram schematically illustrating forming pores included in a method of manufacturing an allogeneic soft-tissue transplant according to an embodiment of the present invention.

Referring to FIG. 1, the method of manufacturing the allogeneic soft-tissue transplant includes forming at least one pore in the allogeneic soft-tissue support in which the immunological rejection cell is removed (step 400). The pore is a part where autologous stem cells, which will be described later, may be loaded. The pore is formed by applying a superfine fiber needle to the allogeneic soft-tissue support. Referring to FIG. 4, a surface of an allogeneic soft-tissue support 10 in which the immunological rejection cell is removed is stimulated by the superfine fiber needle (for example, M100SWBL model, Korea) 420 and at least one pore 410 is formed. The pore 410 may have a size (diameter) in a range from about 1 to about 1,000 micrometer ($\mu m$), and more particularly, may have a size (diameter) of about 10 $\mu m$. The number of pores 410 is not specifically limited, but as many pores as possible may be formed within the surface area of the allogeneic soft-tissue support 10. After the pore 410 has been formed, a substance for supporting the autologous stem cells, which will be described later, may be additionally injected before or after injecting the autologous stem cells. The additionally injected substance may include a growth factor and the like.

Referring to FIG. 1, the method of manufacturing the allogeneic soft-tissue transplant includes injecting autologous stem cells of a user into the pores (step 500). The autologous stem cell refers to stem cells existing in the body receiving the transplant. Stem cells may be defined as cells existing in a status of no differentiation into a specific cell type, but having a potential of dividing and differentiating into various types of cells that constitute a body when needed. The stem cells may be currently being variously applied in the regenerative medicine field, successively replacing or supplementing classical medicinal treatments or surgical treatments. In particular, adult stem cells are cells that constitute specific tissues in a body and that serve to provide a minimum amount of cells for maintaining a normal status when the body is under external effect. In particular, the adult stem cells have little or no immune rejection response in a transplant for organ regeneration, which may have autograft capability. The autologous stem cells according to the present invention may use various stem cells of a body receiving a transplant, the autologous stem cells obtained from a bone marrow of the body that receive the transplant may be used. The autologous stem cells are injected into the pores and become a allogeneic soft-tissue transplant after incubating under suitable conditions, which will be described below.

Referring to FIG. 1, the method of manufacturing the allogeneic soft-tissue transplant includes incubating the allogeneic soft-tissue support in which the autologous stem cells are injected (step 600). The incubating is performed under suitable conditions to change an allogeneic soft-tissue support having the injected autologous stem cells into an allogeneic soft-tissue transplant having optimum transplant conditions. In this regard, the suitable conditions may include a suitable temperature, a suitable pressure, and a suitable duration time. Meanwhile, the incubating (step 600) may further include providing a physical stimulus to the allogeneic soft-tissue support. The providing of the physical stimulus will be described in detail with respect to FIG. 6.

Figure 2:
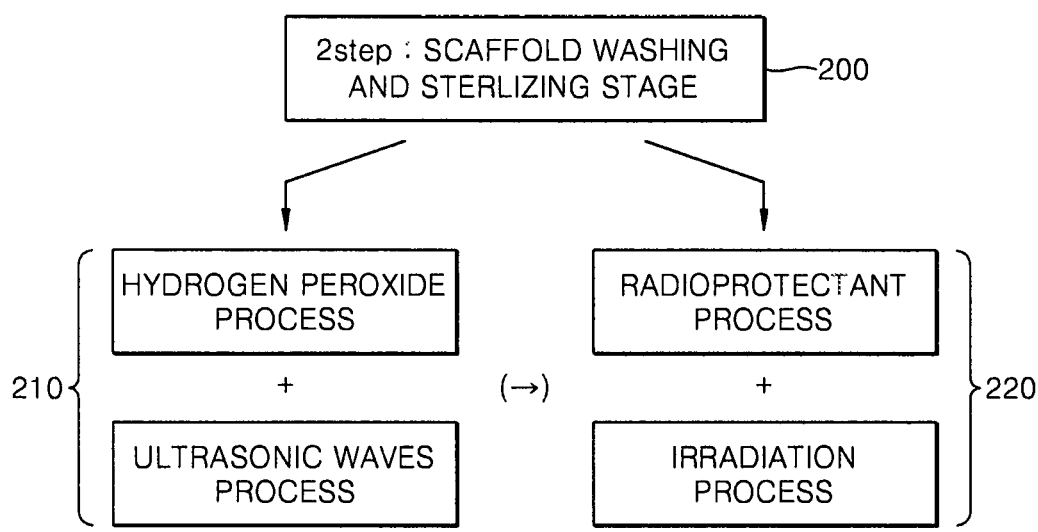
FIG. 2 is a diagram schematically illustrating washing and sterilizing a support used in a method of manufacturing an allogeneic soft-tissue transplant according to an embodiment of the present invention.

FIG. 2 is a diagram schematically illustrating washing and sterilizing a support used in a method of manufacturing an allogeneic soft-tissue transplant according to an embodiment of the present invention.

Referring to FIG. 2, the washing and sterilizing of the obtained allogeneic soft-tissue support (step 200) may include treating the obtained allogeneic soft-tissue support with hydrogen peroxide and applying ultrasonic waves to the obtained allogeneic soft-tissue support (step 210), and treating the obtained allogeneic soft-tissue support with a radioprotectant and irradiating the allogeneic soft-tissue support (step 220)

Due to the treating of the obtained allogeneic soft-tissue support with hydrogen peroxide and applying of ultrasonic waves to the obtained allogeneic soft-tissue support (step 210), both chemical and physical washing and sterilizing effects may be obtained with respect to the allogeneic soft-tissue support. Meanwhile, the treating of the obtained allogeneic soft-tissue support with hydrogen peroxide and applying of the ultrasonic waves to the obtained allogeneic soft-tissue support (step 210) may contribute to fortification of physical properties of the allogeneic soft-tissue support, for example, tension strength, in specific areas. For example, the tension strength of a ligament is increased as a result of treating the hydrogen peroxide having a concentration in a range from about 0.1 to about 5.0% and applying the ultrasonic waves having an output in a range from about 120 to about 400 watt (W) performed on a ligament that is obtained from a human body. Therefore, in regard to the treating of the obtained allogeneic soft-tissue support with the hydrogen peroxide and applying of the ultrasonic waves to the obtained allogeneic soft-tissue support, the hydrogen peroxide used for the treatment may have a concentration in a range from about 0.1 to about 5.0%, and the applied ultrasonic waves may have an output in a range from about 120 to 400 W. In some embodiments, the hydrogen peroxide may have a concentration of about 0.5%, and the applied ultrasonic waves may have an output of 120 W. In addition, a sterilization effect may be maximized by the treating of the obtained allogeneic soft-tissue support with the radioprotectant and irradiating the allogeneic soft-tissue support (step 220). In general, the allogeneic soft-tissue support may be sterilized by irradiation, but an adverse effect from radiation may be minimized by using the radioprotectant. The radioprotectant used for treatment may vary, but cobalt-60 ($Co^{60}$) and the radiation may be selected within various ranges. For example, gamma ray radiation may be in a range from about 12 to about 50 kilogray (kGy). Meanwhile, in regard to the washing and sterilizing of the obtained allogeneic soft-tissue support (step 200), the treating with hydrogen peroxide and applying ultrasonic waves to the obtained allogeneic soft-tissue (step 210) and the treating of the obtained allogeneic soft-tissue support with the radioprotectant and irradiating the allogeneic soft-tissue support (step 220) may be applied separately or simultaneously. Here, in regard to the washing and sterilizing of the obtained allogeneic soft-tissue support (step 200), the obtained allogeneic soft-tissue support is treated with the hydrogen peroxide and applied by the ultrasonic waves (step 210), and then is treated with the radioprotectant and applied by the irradiation (step 220).

Figure 3:
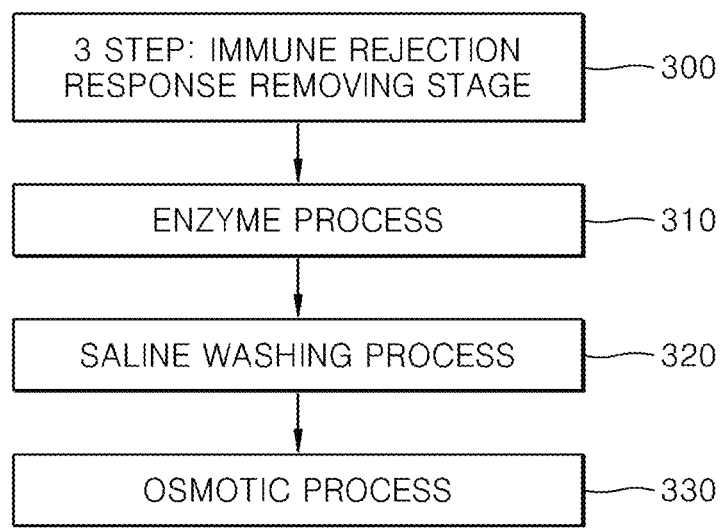
FIG. 3 is a flowchart of removing immunological rejection cells included in a method of manufacturing an allogeneic soft-tissue transplant according to an embodiment of the present invention.

FIG. 3 is a flowchart of removing immunological rejection cells included in a method of manufacturing an allogeneic soft-tissue transplant according to an embodiment of the present invention.

Figure 9A:
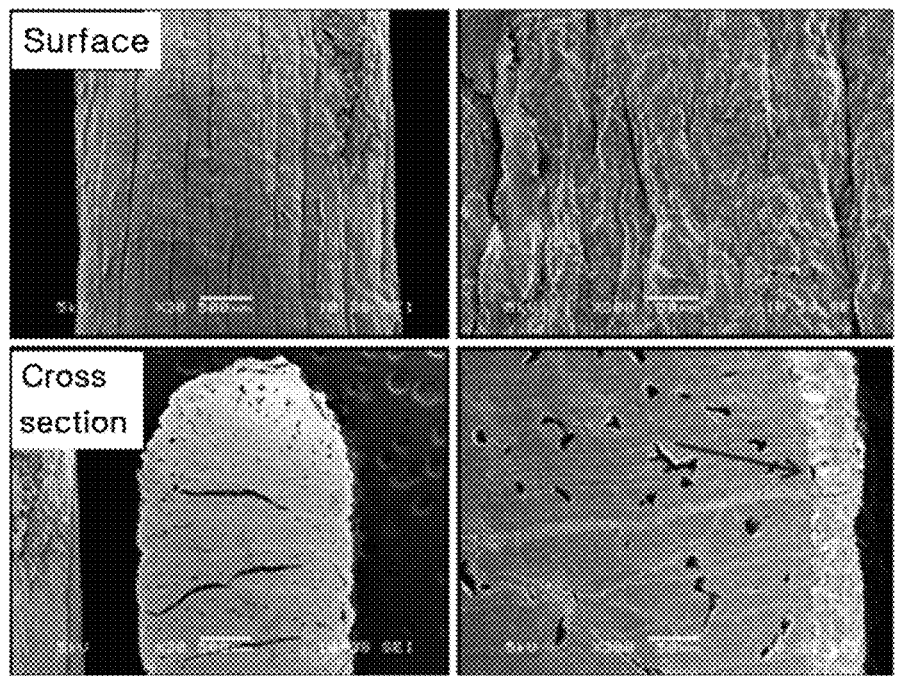
FIGS. 9A and 9B are scanning electron microscope (SEM) images of a surface and a cross-section of an allogeneic soft-tissue support before and after removing of immunological rejection cells included in a method of manufacturing an allogeneic soft-tissue transplant according to an embodiment of the present invention.
Figure 9B:
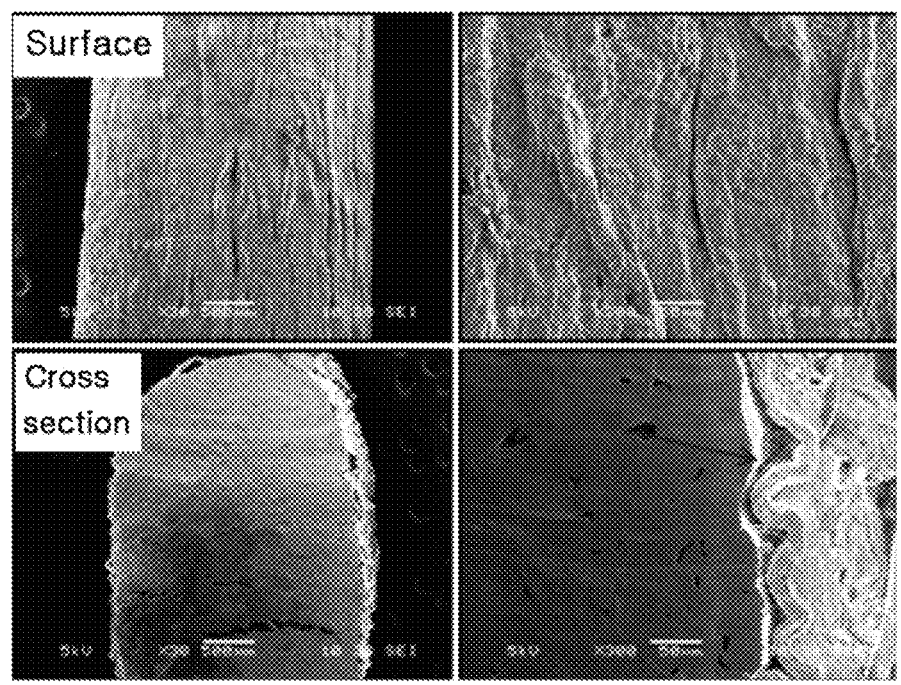
Figure 10A:
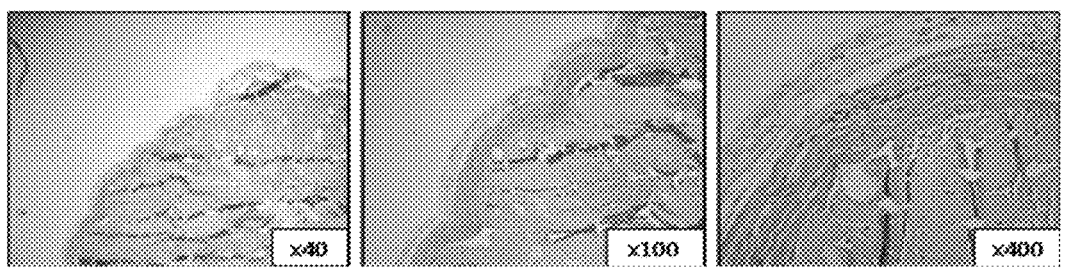
FIGS. 10A and 10B are images illustrating a hematoxylin & eosin dyed cross-section of an allogeneic soft-tissue support before and after removing of immunological rejection cells included in a method of manufacturing an allogeneic soft-tissue transplant according to an embodiment of the present invention.
Figure 10B:
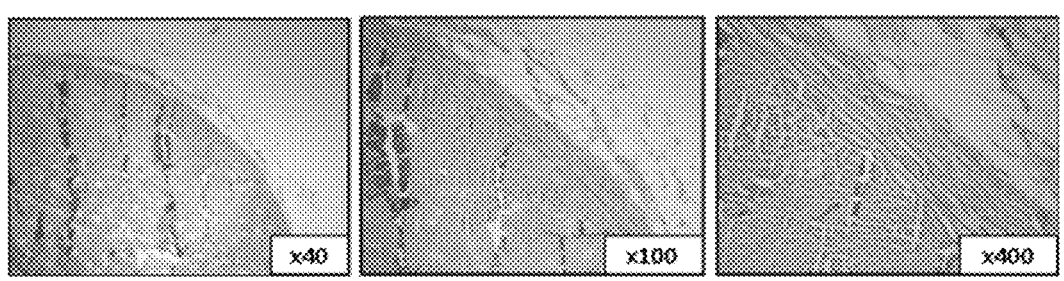
Figure 11:
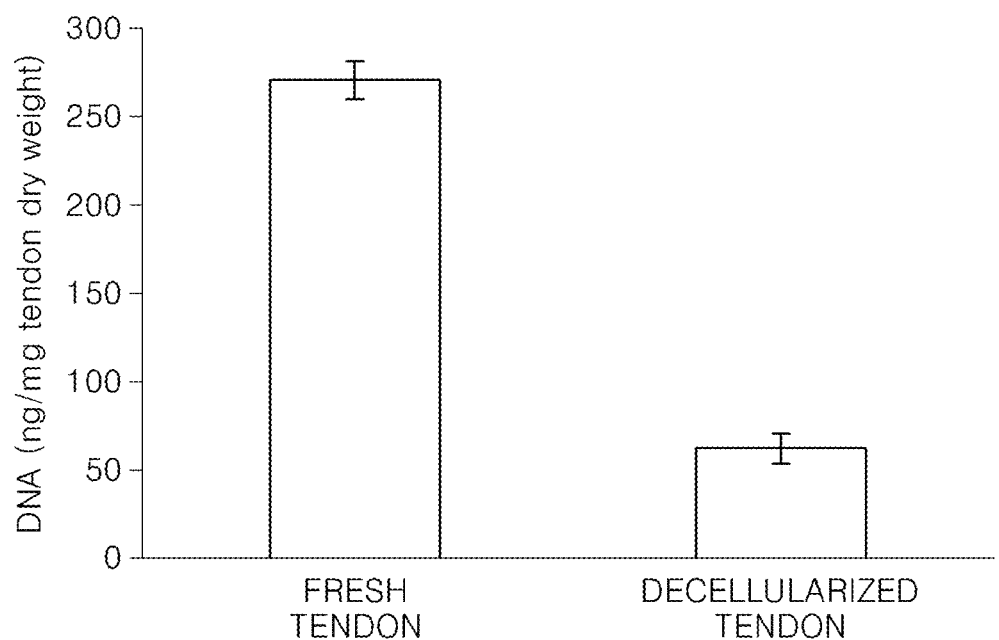
FIG. 11 is a graph illustrating results of DNA residual contents in a pig allogeneic tibialis tendon before and after performing decellular processing according to an embodiment of the present invention.

Referring to FIG. 3, removing immunological rejection cells (step 300) includes treating the allogeneic soft-tissue support with an enzyme solution (step 310) and/or with water washing the sterilized allogeneic soft-tissue support with saline (step 320). The enzyme solution may include various enzymes for the removing of the immunological rejection cells, and in some embodiments, the enzyme solution may contain trypsin, collagenase and protease. For example, the enzyme solution may include about 0.25% of trypsin (0.02% ethylenediaminetetraacetic acid (EDTA), Invitrogen Corp., USA), about 3 mg of collagenase A (0.15 U/mg, Sigma Aldrich, USA), and about 15 mg of protease (4.8 U/mg, Sigma Aldrich, USA), and the enzyme solution may be stirred with about 40 ml of solution at a temperature of 37° C., and at a rate of about 120 rpm for about 4 hours together with the allogeneic soft-tissue support (using Shaking incubator, N-BIOTEK, KOREA). Meanwhile, the water washing of the sterilized allogeneic soft-tissue support with saline is performed to remove any residual enzyme solution. Therefore, the removing of the immunological rejection cells (step 300) may further include water washing with physiological saline (step 320) after treating the washed and sterilized allogeneic soft-tissue support with the enzyme solution (step 310). In addition, the removing of the immunological rejection cells (step 300) may further include washing with distilled water by osmotic treatment (step 330) after the water washing of the allogeneic soft-tissue support with the physiological saline (step 320) after being treated with the enzyme solution (step 310). However, the physiological saline is used for the purpose of washing, and accordingly the quantity and salinity of compositions of the physiological saline are not specifically limited. For example, the physiological saline may be treated with about 40 ml of a solution at a temperature of about 4° C., at a rate of about 120 rpm for about 4 hours together with the allogeneic soft-tissue support, and may be continuously treated for about 12 hours after being treated for about a minute three times. Here, the washing with distilled water by osmotic treatment may be performed after the water washing with the physiological saline, and for example may be ultrasonicated for about 5 minutes with about 240 W output (using Ultra Sonicator, Biofree, Korea). FIG. 9A is a surface and a cross-section of an allogeneic soft-tissue support before removing of the immunological rejection cells included in the method of manufacturing an allogeneic soft-tissue transplant, and FIG. 9B is an SEM image of a surface and a cross section of an allogeneic soft-tissue support after the removing of immunological rejection cells included in a method of manufacturing an allogeneic soft-tissue transplant according to an embodiment of the present invention. In addition, FIG. 10A is an image illustrating a hematoxylin & eosin dyed cross-section of an allogeneic soft-tissue support before removing of immunological rejection cells included in the method of manufacturing an allogeneic soft-tissue transplant, and FIG. 10B is an image illustrating a hematoxylin & eosin dyed cross-section of an allogeneic soft-tissue support after removing of immunological rejection cells included in the method of manufacturing an allogeneic soft-tissue transplant. Referring to FIGS. 9B and 10B, cells of the allogeneic soft-tissue transplant are removed by removing the immunological rejection cells.

Figure 5:
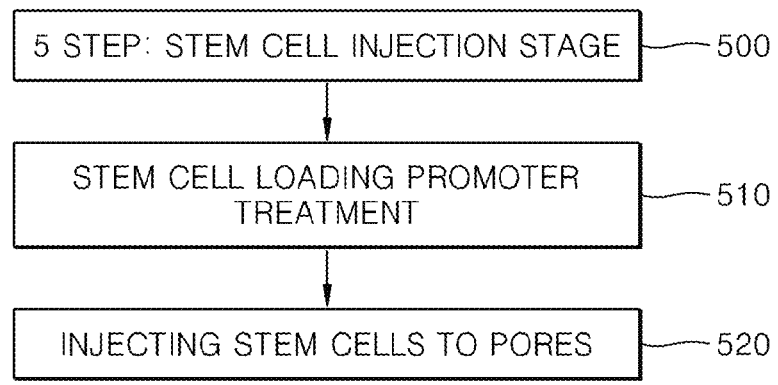
FIG. 5 is a flowchart of injecting autologous stem cells included in a method of manufacturing an allogeneic soft-tissue transplant according to an embodiment of the present invention.

FIG. 5 is a flowchart of injecting autologous stem cells included in a method of manufacturing an allogeneic soft-tissue transplant according to an embodiment of the present invention.

Referring to FIG. 5, the injecting the autologous stem cells (step 500) further includes injecting a supported catalyst for the autologous stem cells (step 510) before or at a time of injecting the autologous stem cells (step 520). The supported catalyst for the autologous stem cells is a substance that is a highly concentrated fluid consisting of soluble proteins existing in bones, such as collagen, gelatine, bone morphogenetic protein-2 (BMP2), BMP4, BMP7, platelet-derived growth factor (PDGF) and transforming growth factor beta (TGF-beta), is freeze-dried and rehydrated into a solution with a fixed viscosity; the solution may induce the autologous stem cells injected into the pore to attach appropriately to the allogeneic soft-tissue support. The supported catalyst for the autologous stem cells is manufactured purely from human bone without any addition of external substances, and accordingly has no immune rejection response to an transplanted body, and is in a physiological active form. Therefore, when the supported catalyst for the autologous stem cells is additionally injected, the autologous stem cells show significant bone delivery capability and bone transfer capability, and easily adapt into the body by maintaining viscosity originated from a collagen constituent.

Figure 6:
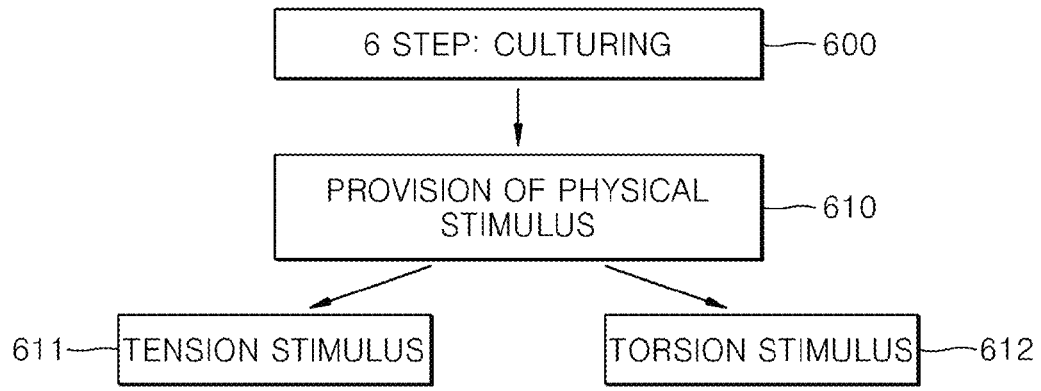
FIG. 6 is a flowchart of providing a physical stimulus in incubating an allogeneic soft-tissue support included in a method of manufacturing an allogeneic soft-tissue transplant according to an embodiment of the present invention.
Figure 7:
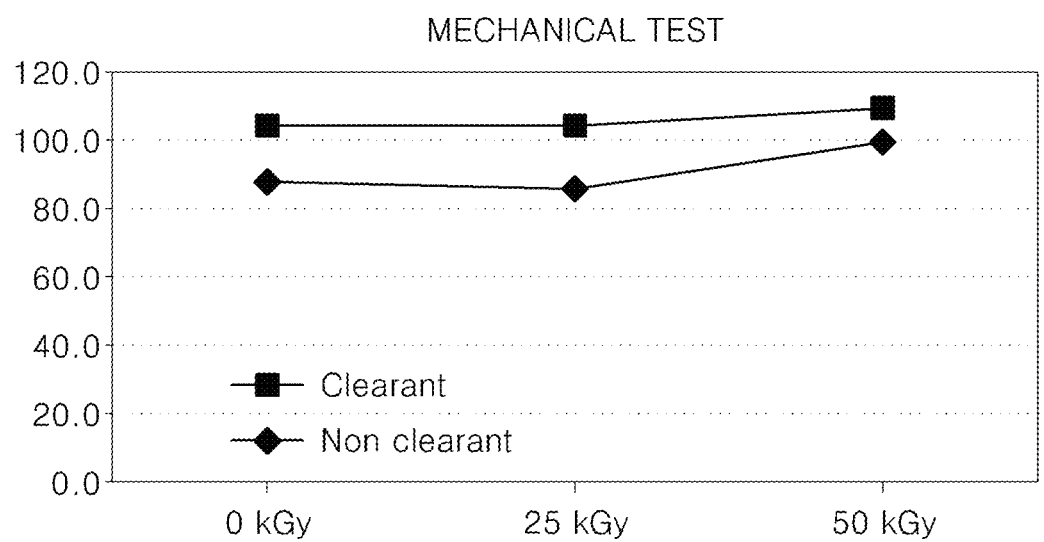
FIG. 7 is a graph illustrating results of tension strength measured before and after performing clearant process treatment with respect to an allogeneic tibialis tendon, according to an embodiment of the present invention.
Figure 8:
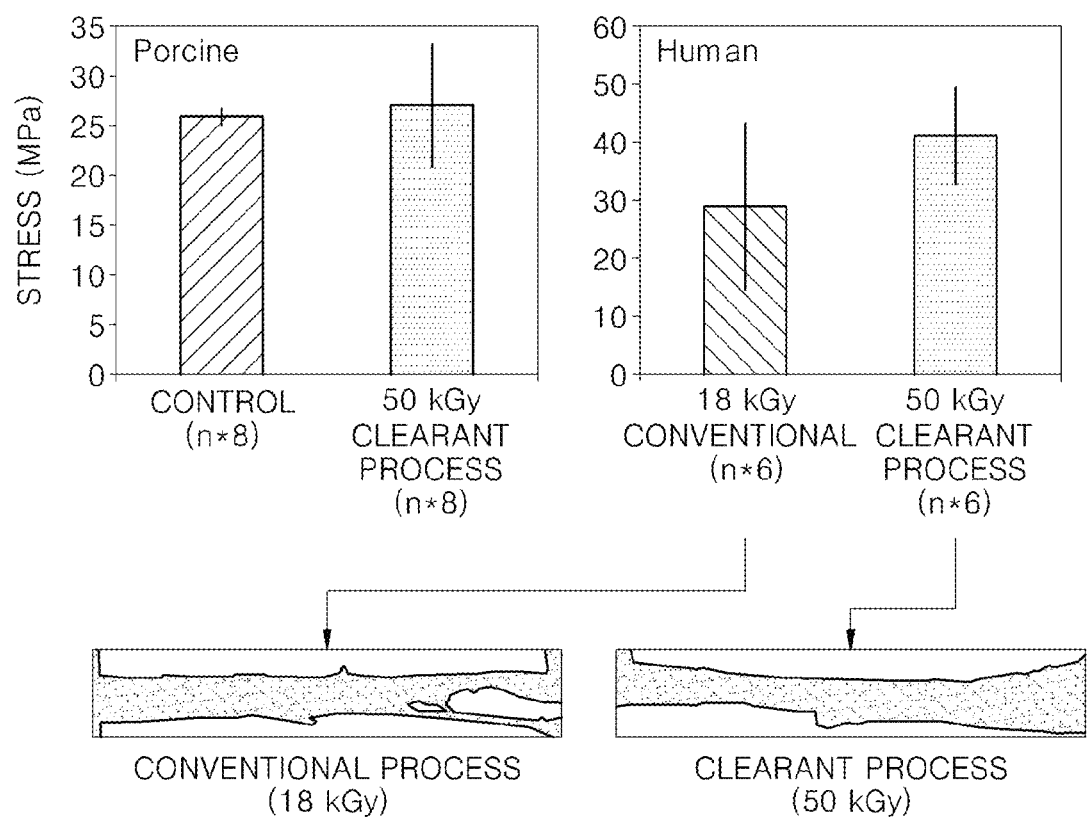
FIG. 8 is a diagram illustrating results of tension strength measured by normal irradiation and by irradiation after performing clearant process treatment with respect to human and pig allogeneic tibialis tendons, according to an embodiment of the present invention.

FIG. 6 is a flowchart of providing a physical stimulus in incubating an allogeneic soft-tissue support included in the method of manufacturing an allogeneic soft-tissue transplant.

Referring to FIG. 6, the incubating of an allogeneic soft-tissue transplant with the injected autologous stem cells (step 600) additionally includes providing a physical stimulus to the autologous stem cell support (step 610). As previously described, the soft-tissues existing in a body may be distributed in sections that support or maintain bodyweight and may serve to support and maintain repetitive movements, such as bending, twisting, and rotation, and consequently, may receive various external stimuli. From the provision of the physical stimulus, efficient histo-differentiation occurs by adding the various external stimuli to the autologous soft-tissue transplant being transplanted to facilitate fusion to original tissues of the transplanted body. Therefore, the physical stimulus may be provided in various ways to be similar with stimuli given to soft-tissues existing in a body, but may be torsion and/or tensile stress related with kinetic stimuli. According to an embodiment of the present invention, the providing of the physical stimulus (step 610) may include providing tensile stress to two opposite distal ends of the allogeneic soft-tissue support (step 611), providing torsion to the allogeneic soft-tissue support in two opposite horizontal directions with respect to a vertical axis of the allogeneic soft-tissue support (step 612), or providing both tensile stress tensile stress to two opposite distal ends of the allogeneic soft-tissue support (step 611) and torsion to the allogeneic soft-tissue support in two opposite horizontal directions with respect to a vertical axis of the allogeneic soft-tissue support (step 612), at the same. Specifically, the providing of the tensile stress to two opposite distal ends of the allogeneic soft-tissue support (step 611) may include extending the two opposite distal ends of the allogeneic soft-tissue support longitudinally, wherein one distal end is extended in a range of 0 to about 10% based on a total length of the allogeneic soft-tissue support and the other distal end is extended in a range of less than 10% based on a total length of the allogeneic soft-tissue support, at the same time, and the providing the torsion to the allogeneic soft-tissue support (step 612) may include rotating the two opposite distal ends of the allogeneic soft-tissue support, wherein one distal end is rotated in a range of 0 to about 45 degrees clockwise and the other distal end is rotated I in a range of 0 to about 45 degrees counterclockwise, at the same time. In addition, a physical stimulus including the tensile stress (step 611) and/or the torsion stimulus (step 612) may be provided at various frequencies, but may be a frequency of less than 1 Hz. Meanwhile, the incubating (step 600) including the providing of the physical stimulus (step 610) may be performed for in various periods of time, but may be performed for less than 7 days. In order to identify whether the allogeneic soft-tissue support may have a similar strength as a normal tissue of a human body based on providing the physical stimulus, a pig's ligament tissue is obtained and examined. About 10% tensile stress (pulling the twp opposite distal ends by about 5%) and an about 90 degrees of torsion stimulus (twisting one distal end by 45 degrees clockwise, and the other distal end with 45 degrees counterclockwise) were provided at 1 Hz frequency for 1 day, 4 days, and 7 days, and strengths thereof were each measured. As a result, the maximum load (Newton, N) was about 354.9 N for a control group with no stimulus provided, 380.8 N for an experimental group with a stimulus provided for a day, 418.6 N for an experimental group with a stimulus provided for 4 days, and 818.1 N for an experimental group with a stimulus provided for 7 days. From the result value, it was identified that the strength of the pig's ligament tissue provided with continuous tensil stress and torsion stimulus may reach an approximate level similar to a normal tissue of a human body.

Figure 13:
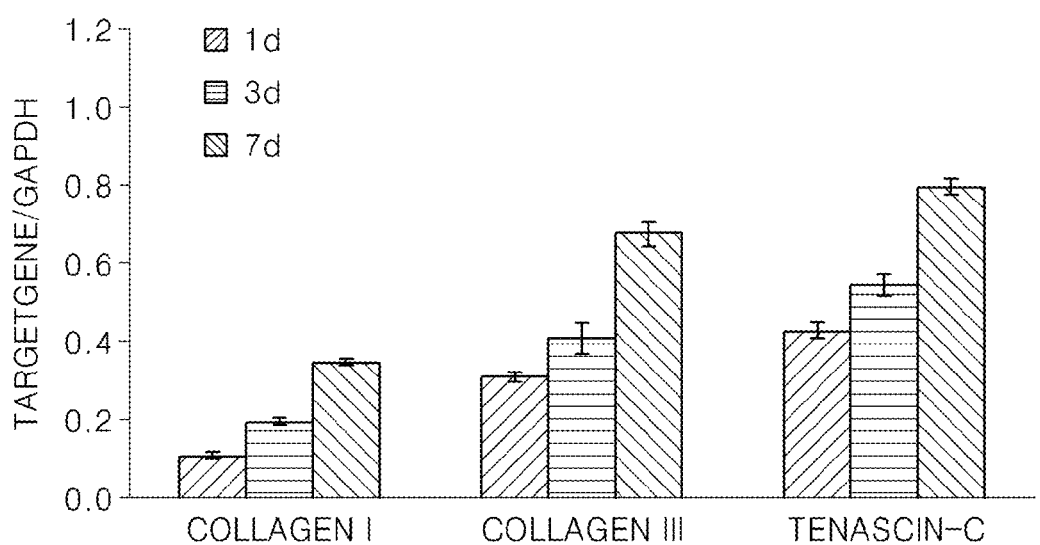
FIG. 13 is a graph illustrating results of real time polymerase chain reaction (PCR) analysis for a stem cell loaded gel transplanted in a tibialis tendon before and after providing a physical stimulus in an incubator according to an embodiment of the present invention.

FIG. 13 is a graph illustrating results of real time polymerase chain reaction (PCR) analysis for a stem cell loaded gel transplanted in a tibialis tendon before and after providing a physical stimulus in an incubator according to an embodiment of the present invention.

Specifically, it is a result of analysis of the real time PCR of collagen type I, type III and tenascin-c gene of a stem cell loaded gel transplanted in the tibalis tendon with the physical stimulus provided for a day, 3 days and 7 days in an incubator. The collagen type I gene increased by 3 times for day 1 and day 7, 0.11±0.01 and 0.34±0.02 respectively. The collagen type III gene increased by 2.2 times for day 1 and day 7, 0.31±0.01 and 0.67±0.03 respectively. The tenascin-C gene increased by 1.9 times for day 1 and day 7, 0.42±0.01 and 0.79±0.02 respectively. The increase of the tenascin-C gene, a representative marker of a ligament tissue, was identified, and it was identified that a mesenchymal stem cell originated from human bone marrow that received physical stimulus was differentiated into a ligament tissue.

Figure 14A:
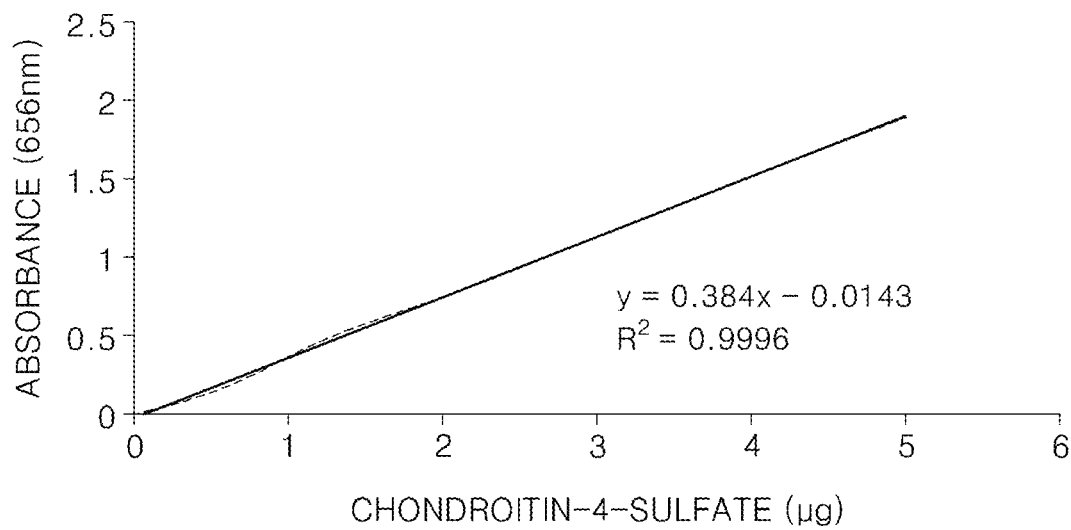
FIGS. 14A and 14B are graphs illustrating results of glycosaminoglycan (GAG) content analysis for a stem cell loaded gel transplant group provided with a physical stimulus in an incubator according to an embodiment of the present invention.
Figure 14B:
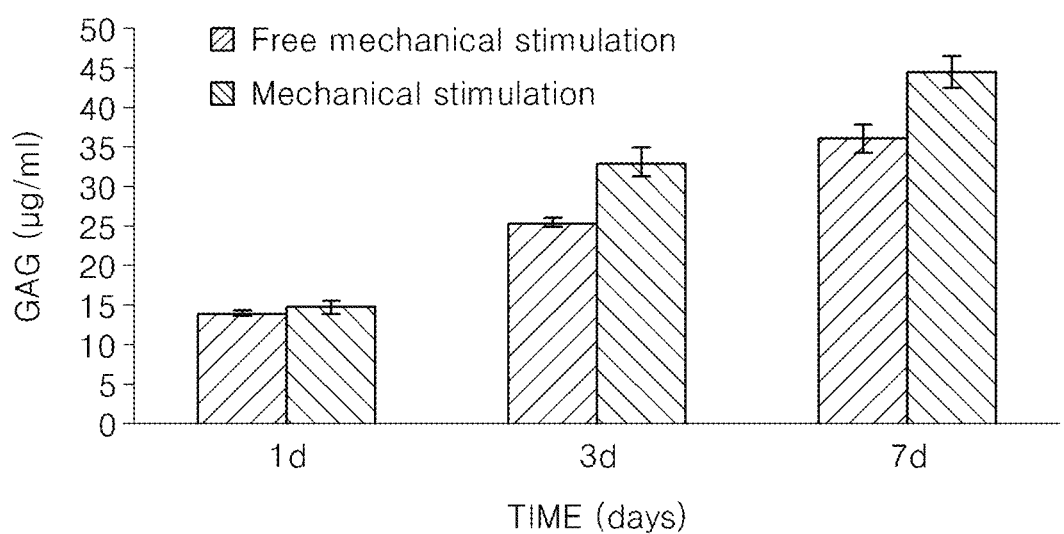

FIGS. 14A and 14B are graphs illustrating results of glycosaminoglycan (GAG) content analysis for a stem cell loaded gel transplant group provided with a physical stimulus in an incubator according to an embodiment of the present invention.

Specifically, analysis of content of GAG secreted from a culture medium of a group with physical stimulus provided in an incubator and a group without the physical stimulus provided, categorized from a stem cell loaded gel transplanted group ($5 \times 10^5$ cells/cm$^2$) inoculated on a surface of a pig's tibialis tendon, was conducted. Culture media after incubating for 1, 3 and 7 days were collected and light absorbance at a wavelength of 656 nm was measured using a GAG assay kit. The linear regression value for a standard chondroitin-4-sulfate curve was 99.9%. The group with the physical stimulus provided showed higher GAG content than the group without the stimulus provided, and the group without the physical stimulus provided was 14.187±0.080 µg/µl on day 1, 25.542±0.599 µg/µl on day 3, 36.346±0.843 µg/µl on day 7, and the group with the physical stimulus resulted with 14.986±0.765 µg/µl on day 1, 33.298±0.936 µg/µl on day 3, 44.791±0.087 µg/µl on day 7, showing an increasing tendency. As a result, a stem cell loaded gel transplanted group having been cultured for 7 days with the physical stimulus provided was increased by about 23% when compared with the group without the stimulus provided.

Figure 15A:
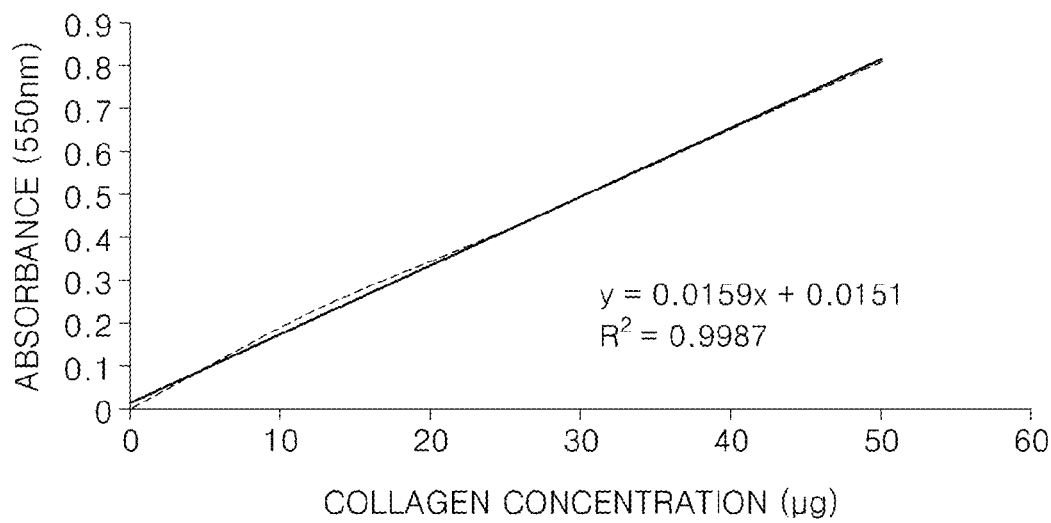
FIGS. 15A and 15B are graph illustrating results of collagen content analysis for a stem cell loaded gel transplant group provided with a physical stimulus in an incubator according to an embodiment of the present invention.
Figure 15B:
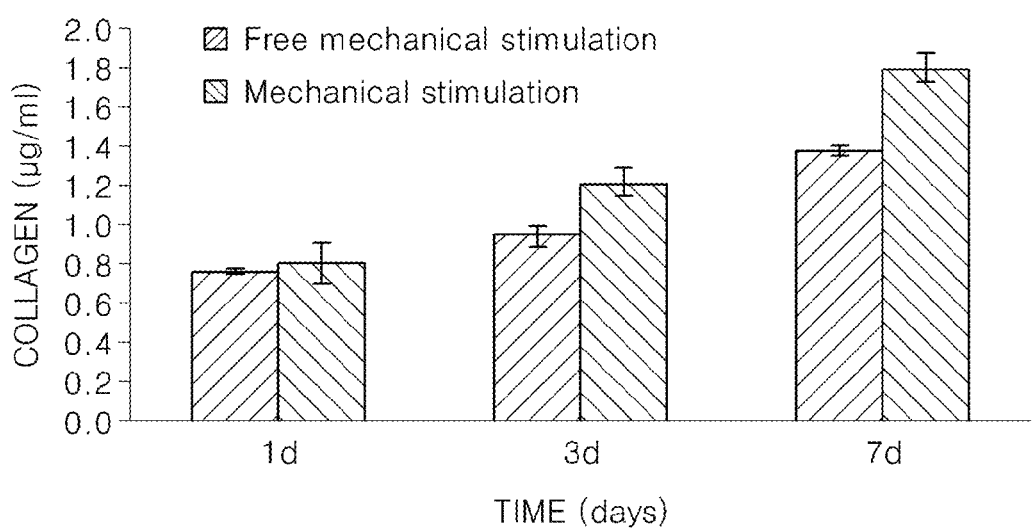

FIGS. 15A and 15B are graph illustrating results of collagen content analysis for a stem cell loaded gel transplant group provided with a physical stimulus in an incubator according to an embodiment of the present invention.

Specifically, analysis of content of collagen secreted from a culture medium of a group with physical stimulus provided in an incubator and a group without the physical stimulus provided, categorized from a stem cell loaded gel transplanted group ($5 \times 10^5$ cells/cm$^2$) inoculated on a surface of a pig's tibialis tendon, was conducted. Culture media after incubating for 1, 3 and 7 days were collected and light absorbance at a wavelength of 550 nm was measured using a GAG assay kit. The linear regression value for a standard collagen curve was 99.9%. The group with physical stimulus provided showed higher collagen content than the group without the stimulus provided, and the group without the physical stimulus provided was 0.769±0.012 µg/µl on day 1, 0.949±0.052 µg/µl on day 3, 1.382±0.028 µg/µl on day 7, and the group with the physical stimulus resulted with 0.811±0.106 µg/µl on physical stimulus day 1, 1.218±0.072 µg/µl on day 3, 1.803±0.065 µg/µl on day 7, showing an increasing tendency. As a result, a stem cell loaded gel transplanted group having been cultured for 7 days with the physical stimulus provided was increased by about 30% when compared with the group without the stimulus provided.

Mode of the Invention

One or more embodiments will be described in further detail with reference to the following examples. However, these examples are for illustrative purposes only and are not intended to limit the scope of the invention.

Example 1

Sterilization of an Allogeneic Soft-Tissue Support

A patella and a tibia of a pig were acquired to collect a soft-tissue support. After treating tissues with chemicals, the collected soft-tissue support was sterilized by using a Clearant Process® (US2005/U.S. Pat. No. 6,908,591B2), an apparatus used for high dose gamma ray sterilization. Specific methods used are as follows.

16.2% propylene glycol, 22.1% DMSO, 2.7% mannitol, 3.8% tetrahalose, and 60.0% purified water were mixed to manufacture a radioprotectant solution. The allogeneic ligament to be sterilized was placed in a sterilizing pouch, a manufactured solution proportional to the weight of the tissue was added, and thermal shrinkage packaging was performed. After treating with chemicals based on Clearant Process® protocols, moisture of the tissues was removed with a sterile towel (20-30% moisture remaining), and the tissues were freeze-dried and were then packed and freeze-stored. A total elapsed time for chemical treatment of the tissues was 25 hours, and afterwards an additional 24 hours elapsed for the stored freeze-dried tissues. Also, sterilization was performed using gamma rays (0, 25, 50 KGy). It was identified that bones that received irradiation after the Clearant treatment had increased tension strength when compared with bones with regular irradiation Example 2

Immune Rejection Response Inhibition of Allogeneic Soft-Tissue Support

Example 2-1

Decellularization of Soft-Tissue Support for Inhibiting Immune Rejection Response A decellularization process was performed for removing tissue antigens from cellular components in soft-tissue supports that went through washing and sterilizing processes. The decellularization process was performed using an enzyme solution treatment, a water washing treatment and an osmotic treatment, and the specific methods used are as follows.

A pig's tibialis tendon (12 cm length, 1 cm width) frozen in a −70° C. deep freezer was taken out and placed in sterile distilled water, and was melted for 30 minutes in a 37° C. water bath (DongA, KOREA) for the enzyme solution treatment. 10 tibialis tendons were placed in a 1,000 ml beaker with 500 ml of an enzyme cocktail solution [0.25% trypsin (T4049, SIGMA, USA) 500 ml, collagenase A (C0130, SIGMA, USA) 37.5 ml, protease (P4630, SIGMA, USA) 187.5] after melting, and were stirred for 4 hours at 120 rpm, and at 37° C. in a shaker incubator (NB-205V, N-BIOTEK, KOREA).

An enzyme cocktail solution was removed after 4 hours for water washing and 500 ml of physiological saline was added. Afterwards washing was performed for an hour while stirring in the shaker incubator at 120 rpm, and at 4° C. The process was repeated three times, and the last washing process was performed for 12 hours.

Physiological saline was removed after 12 hours for osmotic treatment, and 500 ml of sterile distilled water was added. Afterwards treatment was performed for 5 minutes at 240 W using an ultrasonicator. Sterile distilled water was removed, 500 ml of physiological saline was added and treatment was performed for 5 minutes at 240 W using the ultrasonicator.

Example 2-2

SEM Image of a Decellularized Scaffold

An external form of a pig's tibialis tendon tissue before and after decellularization was identified through an SEM image (5 kV, JSM-6380, Jeol Inc., JAPAN). The specific methods used are as follows. The washed and sterilized pig tibialis tendon acquired was washed with a 1 M phosphate salt buffer (70011, GIBCO, USA, pH 7.4). Afterwards, fixation was performed by adding a 2.5% glutaraldehyde (340855, SIGMA, USA) solution and the fixation was performed for 24 hours at 4° C. Washing was performed with sterilized PBS and dehydration was performed by running for an hour with each increased concentration of alcohol at 50, 70, 80, 90 and 100%. The dehydrated tissue was placed in a humidistat (Dry keeper, Sanplatec, JAPAN) and was dried at room temperature. The dried tissue was fixed on a section fixing stage using double-sided tape, and platinum with 200 Å thickness was coated by using a plasma sputter. Afterwards the external shape of the tissue was observed in 30× and 300× magnification using a low magnifying SEM.

Example 2-3

Histological Staining of a Decellularized Scaffold

Cellular nucleus and cytoplasm were stained with hematoxylin and eosin and a distribution trend and an exterior figure of cells existing in the tibialis tendon were identified. The specific methods used are as follows.
Preprocessing for tissue staining was performed as follows.
Tissue process (STP 120, Thermo scientific, USA) equipment was used under the following program conditions.

TABLE 1

| Reagent Container No. | Reagent | Immersion time Unit: Min. | Stirring rate RPM | Programmed value |
|---|---|---|---|---|
| 1 | Formalin | 12:00 | 60 | 1 |
| 2 | Formalin | 12:00 | 60 | 1 |
| 3 | Alcohol 70% | 01:30 | 60 | 1 |
| 4 | Alcohol 80% | 01:30 | 60 | 1 |
| 5 | Alcohol 95% | 01:30 | 60 | 1 |
| 6 | Alcohol 100% | 01:00 | 60 | 1 |
| 7 | Alcohol 100% | 01:00 | 60 | 1 |
| 8 | Alcohol 100% | 01:00 | 60 | 1 |
| 9 | Xylene | 01:30 | 60 | 1 |
| 10 | Xylene | 01:30 | 60 | 1 |
| 11 | Paraffin | 02:00 | 60 | 1 |
| 12 | Paraffin | 02:00 | 60 | 1 |

In order to manufacture a tissue block sample section, a tissue immersed in a paraffin solution was put in a tissue embedding system (Histocentre 3, Thermo, USA) after placing a mold base on a hot plate of the system and pouring in some of the paraffin first. Afterwards, the remaining paraffin was poured in. The paraffin block was hardened for 10 minutes on the cold plate of the tissue embedding system and was stored at room temperature after removing the mold base.

A microtome (Finess met, Thermo, USA) and a microtome blade were used to perform trimming work in 10 μm thickness and tissue sections were made in 4 μm thicknesses to make tissue slides. The sections were floated on a container with tap water, scooped out with slides, floated on a preheated water bath and were dried at 60° C. after attaching tissue sections on each slide.

H&E staining was performed afterwards. The detailed staining methods are as follows.

To perform a deparaffin process, a tissue slide was immersed three times in a glass stain jar with xylene for 10 minutes each time. To perform a hydration process, the tissue slide was immersed for 5 minutes in the first glass stain jar with 99.9% alcohol. The tissue slide was moved to the second glass stain jar with 99.9% alcohol and was immersed for 5 minutes. The tissue slide was moved to the second glass stain jar with 95% alcohol and was immersed for 3 minutes. The tissue slide was moved to the second glass stain jar with 80% alcohol and was immersed for 3 minutes. The tissue slide was moved to the second glass stain jar with 70% alcohol and was immersed for 3 minutes. The tissue slide was moved to flowing tap water and was immersed for 1 minutes.

To perform a nuclear stain process, the slide was immersed in Harris hematoxylin for 10 minutes and was moved to flowing tap water and was immersed for 3 minutes.

To perform a decolorizing process, the slide was tapped 3 times in a glass stain jar with 1% alcoholic HCl and the slide was moved to flowing tap water and was immersed for 3 minutes. For a neutralization process, the slide was moved to a glass stain jar with 1% ammonia water and was immersed for 1 minutes, and was moved to flowing tap water and was immersed for 3 minutes. To perform cytoplasm staining, the slide was moved to eosin and was immersed for a minute. Afterwards, the slide was dehydrated by tapping in a glass stain jar with 70% alcohol. Afterwards, the tissue slide was immersed in a glass stain jar with clear xylene for 15 minutes. Afterwards a forceps was used to put a drop of mount solution on the tissue slide, a cover glass was used to cover it and photographs were taken with a microscope.

Example 2-4

Measurement of DNA Residual Content of a Decellularized Base

A pig tibialis tendon was frozen for 24 hours at −20° C. before and after decellularization, and a freezing dryer was used to remove moisture. Afterwards, residual DNA was examined to identify the quantity of remaining cells.

DNA content was measured using a DNEasy kit (69506-250, Qiagen, USA). The detailed methods used are as follows. 25 mg of a freeze-dried tissue before and after decellularization was put in a 1.5 ml centrifuge microtube, and 180 μl of ATL buffer was added. 20 μl of Proteinase K was added to the tube, stirred, and the tube was left on a heating block at 55° C. until the tissues were completely degraded (stirring was performed once every two hours). After confirming the degradation, a vortex mixer was used to mix the solution for 15 seconds. 200 μl of AL buffer was added to the tube, was mixed by using the vortex mixer, and was left on the heating block for 10 minutes at 70° C. 200 μl of 99.9% alcohol was added to the tube and was mixed by using the vortex mixer. The mixed sample was put in a DNeasy spin column joined to a 2 ml collection tube, and centrifugation was performed (8,000 rpm) for a minute and the fluid filtered in the collection tube was removed. 500 μl of AW1 buffer was added to the DNeasy spin column joined to a 2 ml collection tube and centrifugation was performed (8,000 rpm) for a minute and the fluid filtered in the collection tube was removed. 500 μl of AW2 buffer was added to the DNeasy spin column joined to a 2 ml collection tube and centrifugation was performed (17,000 rpm) for 3 minutes to ensure a DNeasy membrane was completely dried. The fluid attached to the DNeasy spin column was identified, and centrifugation (17,000 rpm) was performed for another minute if the attachment was found. The DNeasy spin column with the dried DNeasy membrane was joined to a new 1.5 ml centrifuge microtube, 200 μl of AE buffer was added and was left for a minute at room temperature. Afterwards centrifugation (8,000 rpm) was performed for a minute, and the fluid collected in the 1.5 ml centrifuge microtube was used for the experiment. The collected fluid was measured using a DNA quantification program of Nanodrop (nanodrop 2000, thermo, USA). The result, having identified that a tibialis tendon with decellularization shows significantly low DNA residual content, was as follows.

TABLE 2

| Sample | DNA residual content (ng/mg) |
|---|---|
| Tibialis tendon without decellularization | 269.9 ± 10.9 |
| Tibialis tendon with decellularization | 62.7 ± 8.5 |

Example 3

Injection of Stem Cells Using Autologous Stem Cell Loading Promoter

Example 3-1

Manufacture of Cell Loading Promoter

To inject autologous stem cells into a tibialis tendon with autologous stem cells, a cell loading promoter was manufactured under the following method.

Collagen gels extracted from pig skin by treating with pepsin in a sterile process system were purchased from Bioland Co., and more than 99% of the collagen was identified to be in a type I form as a result of reviewing the examination report.

A recomposition buffer for coagulating a collagen solution was produced by dissolving 2.2% $NaHCO_3$ (90421-C, SAFC Bioscience, USA) and 200 mM HEPES (H4034, SIGMA, USA) in a 0.05 N NaOH solution, and the total volume was set to be 100 ml. A 0.2 μm syringe filter (16534, Satorius stedim, USA) was used to filter and sterilize the solution, and the solution was stored at 4° C. until used. A PBS solution was filtered and sterilized by using a 0.2 μm syringe filter, and was stored at 4° C. until used.

The composition of the final collagen solution was achieved by mixing acid-soluble collagen gel solution:PBS (10× concentrated solution):recomposition purposed buffer at a ratio of 8:1:1. The mixing was done in a Styrofoam box with ice to prevent the neutral collagen gel from quick gelation.

Example 3-2

Identification of Growth Rate of Autologous Stem Cells in Cell Loading Promoter The mesenchymal stem cells that originated from human bone marrow, which were collected after centrifugation, were separated into $1\times10^5$, $2\times10^5$ and $5\times10^5$ cell/cm² groups, and were mixed with the manufactured neutral collagen gel by pipetting slowly to prevent bubbling. The cell loaded collagen gel was inoculated on 48-well culture plate dishes by 150 μl each, and was left for an hour in an incubator (NB-203XLSP, N-BIOTEK, KOREA) at 37° C., under 5% CO2 conditions. The gelation was identified after an hour (translucent), and 200 μl of a-MEM (12571, GIBCO, USA) with 10% FBS (16000, GIBCO, USA) and 1% penicillin-streptomycin (15140, GIBCO, USA) was added for each. Afterwards incubating was performed at 37° C., in a 5% $CO_2$ incubator.

Figure 12A:
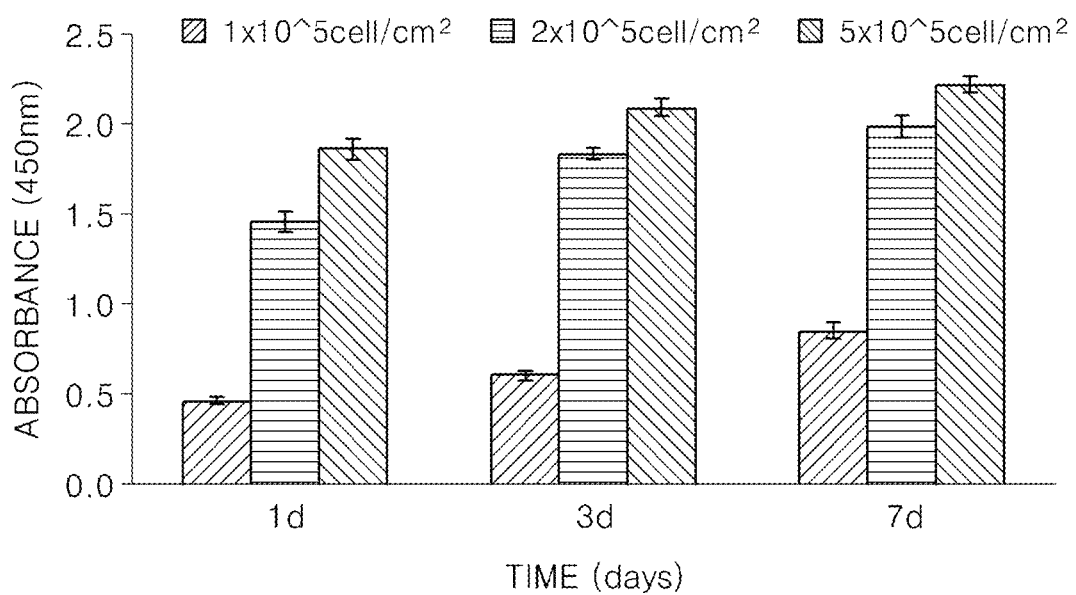
FIGS. 12A and 12B are graphs illustrating results of cell growth rates on the first, third, and seventh day of incubation with respect to (A) stem cell loaded collagen gel (0.5%) and (B) stem cell support collagen gel (1.0%) in $1 \times 10^5$, $2 \times 10^5$ and $5 \times 10^5$ cells/cm$^2$ concentrations according to an embodiment of the present invention.
Figure 12B:
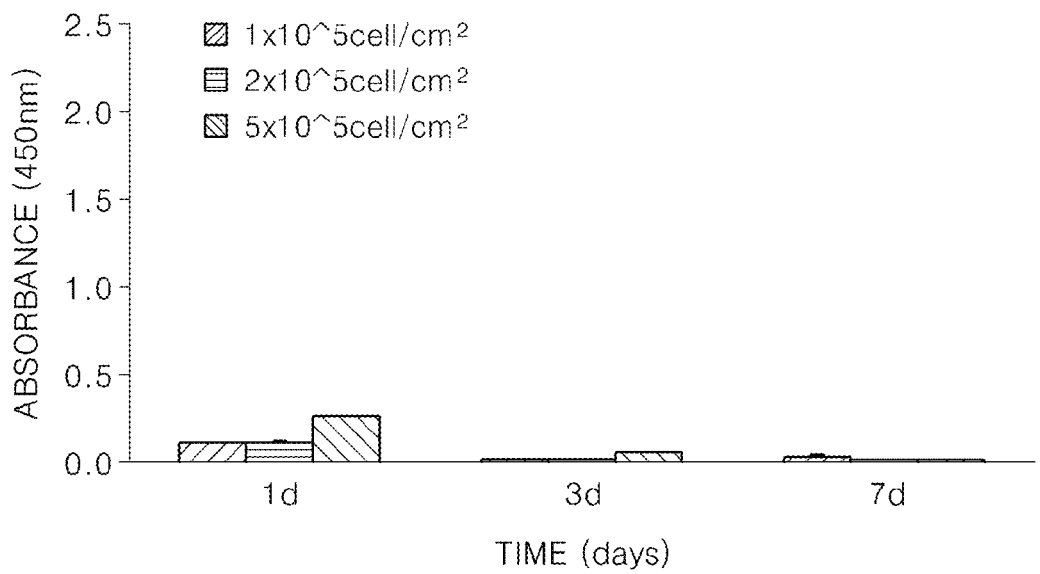

Cell survival rate at stem cell loaded collagen gel incubating day 1, 3 and 7 based on collagen gel concentration (0.5, 1.0%) and the number of human bone marrow originated mesenchymal stem cells ($1\times10^5$, $2\times10^5$ and $5\times10^5$ cells/cm²) were measured. The detailed measurement methods are as follows. A vial (5 ml) stored in an EZ Cytox assay kit (Cat. no EZ3000, DAIL LAB, KOREA) was taken out and was placed on a clean bench. 3 ml of a-MEM with 10% FBS and 1% (penicillin-streptomycin) was added to a 15 ml conical tube by using a pipette and 300 μl of an EZ Cytox reagent was added and mixed. The cell culture used for incubating the stem cell loaded collagen gel was removed by vacuum suction, and 200 μl of cell culture with EZ Cytox reagent mixed was added to each well of a 48-well culture plate dish. Incubating was done for an hour at 37° C., in a 5% $CO_2$ incubator. Light absorbance at a wavelength of 450 nm was measured by using an ELISA reader (1420, PerkinElmer, USA) (refer to FIGS. 12A and 12B).

Example 3-3

Injection of the Manufactured Neutral Collagen with Autologous Stem Cells to Pores Pores were formed by applying a superfine fiber needle (M100SWBL model, KOREA) to the decellularized tibialis tendon to inject autologous stem cells. The diameter of the pores was about 10 micrometer (μm). The stem cell loaded collagen gel manufactured in the <Example 3-2> was injected into the tibialis tendon in which the pores were formed.

Example 4

Soft-Tissue Support Culture Using Physical Stimulus

Example 4-1

Soft-Tissue Support Culture with Physical Stimulus

A comparative analysis was done on a physical strength tendency of a stem cell loaded gel transplant that has been inoculated in a tibialis tendon based on a physical stimulus condition and time setting in an incubator. That is, the following methods were performed to identify an influence on enhancement of transplants' strength. A section was prepared to have a size of 12×1 cm² (width×length) and was placed in a chamber. For an experimental group, the experiment was performed by providing a physical stimulus for 1, 3 and 7 days in an incubator at a frequency of 1 Hz of a 10% (2 mm for each terminal) tensile stress and a 90° (45° clockwise and counterclockwise for each) torsion stimulus (Table 3). A control group was cultured for 7 days without any physical stimulus in an incubator chamber.

TABLE 3

| | | Physical stimulus condition | | | | | | |
|---|---|---|---|---|---|---|---|---|
| | | Tension (10%) | | Torsion (90°) | | Frequency | | Collecting | N |
| Group | | Top | Bottom | Top | Bottom | Top | Bottom | period | number |
| Control Group | | — | — | — | — | — | — | 7 days | 3 |
| Experimental Group | 1 | 2 mm | 2 mm | 45° | 45° | 1 Hz | 1 Hz | 1 day | 3 |
| | 2 | 2 mm | 2 mm | 45° | 45° | 1 Hz | 1 Hz | 4 days | 3 |
| | 3 | 2 mm | 2 mm | 45° | 45° | 1 Hz | 1 Hz | 7 day | 3 |

Example 4-2

Real-Time PCR Analysis of a Stem Cell Loaded Gel Transplanted Group with Physical Stimulus mRNA was analyzed to analyze a gene expression tendency followed by cell differentiation in a transplant group with a physical stimulus. RNA was extracted by using an RNeasy mini kit (74136, Qiagen, USA). 600 µl of an RLT Plus buffer was added to 30 mg of collected tissue and homogenization was performed. Centrifugation was performed for 3 minutes at a maximum rpm and a supernatant was carefully removed with a pipette. A gDNA eliminator spin column was put on a 2 ml collection tube and the dissolved tissue after homogenization was added. Centrifugation was performed for 30 seconds at 10,000×g and the column was removed while the extracted fluid remained. 600 µl of 70% ethanol was added to the collection tube and was mixed with a pipette. An RNeasy spin column was put on a new 2 ml collection tube and 1,000 µl of a mixed solution was added. A lid was closed, centrifugation was done for 15 seconds at 10,000×g and the extracted fluid was removed. 700 µl of RW1 buffer was added to the RNeasy spin column, centrifugation was performed for 15 seconds at 10,000×g and the extracted fluid was removed. 500 µl of RPE buffer was added to the RNeasy spin column, centrifugation was performed for 15 seconds at 10,000×g and the extracted fluid was removed. 500 µl of RPE buffer was added to the RNeasy spin column, centrifugation was performed for 2 minutes at 10,000×g and the extracted fluid was removed. The RNeasy spin column was put on a new 1.5 ml collection tube, 50 µl of RNase-free water was added to a spin column membrane, and centrifugation was performed for a minute at 10,000×g.

A SuperScript®VILO cDNA Synthesis Kit (11754-050, Invitrogen, USA) was used for synthesizing cDNA and the methods used are as follows. 4 µl of 5× VILO Reaction Mix, 2 µl of 10× SuperScript Enzyme Mix and 2.5 µg of RNA were mixed and DEPC-treated water was added to set the final volume to be 20 µl. The mixed reagent was incubated for 10 minutes at 25° C., 60 minutes at 42° C., and was reacted for 5 minutes at 85° C. and was ended. The solution was stored in a −20° C. freezer until used.

Afterwards, SYBR® Premix Ex Taq (RR420Q, TaKaRa, JAPAN) was used for Real time PCR, and the methods used are as follows. 12.5 µl of SYBR® Premix Ex Taq (1×), 0.5 µl of 0.2 uM PCR Forward Primer, 0.5 µl of 0.2 uM PCR Reverse Primer, 2.0 µl of cDNA synthesizing sample and 9.5 µl of DW water were mixed to set the total volume to be 25 µl. A real time PCR instrument (TP800, TaKaRa, JAPAN) was used and step 1 was to run for 30 seconds at 1 cycle, 95° C., and step 2 was to run for 5 seconds at 95° C. and 30 seconds at 60° C. with 40 cycles. Collagen type I, type III and tenascin-c were used for primers (Table 4).

TABLE 4

| Genes | Forward primer sequences | Reverse primer sequences |
|---|---|---|
| Collagen I | 5'-CAGGGTGTTCCTGGAGACCT-3' (SEQ ID NO: 1) | 3'-AGGAGAGCCATCAGCACCT-5' (SEQ ID NO: 2) |
| Collagen II | 5'-GAAAATGGAAAACCTGGGGA-3 (SEQ ID NO: 3) | 3'-CACCCTTTGGACCAGGACT-5' (SEQ ID NO: 4) |
| Tenascin-C | 5'-TACAGCCTGGCAGACCTGAG-3 (SEQ ID NO: 5) | 3'-ATTGCTTGGGAGCAGTCCT-5' (SEQ ID NO: 6) |
| GAPDH | 5'-AAGGGTCATCATCTCTGCCC-3 (SEQ ID NO: 7) | 3'-GTGATGGCATGGACTGTGGT-5' (SEQ ID NO: 8) |

Example 4-2

GAG Analysis of a Stem Cell Loaded Gel Transplanted Group with Physical Stimulus Content analysis was run for GAG secreted from a culture medium of a group with a physical stimulus in an incubator and a group without the physical stimulus categorized from a stem cell loaded gel transplanted group ($5 \times 10^5$ cells/cm$^2$) inoculated on a surface of a pig's tibialis tendon. Culture media after incubating for 1, 3 and 7 days were collected and GAG (Glycosaminoglycan) content analysis was performed by using a GAG assay kit. The detailed methods used are as follows. Sulfated Glycosaminoglycan (0~5 µg) was used as a standard reagent and was added to a microcentrifuge tube, and a final volume was set to be 100 µl by using purified water. Culture media of stem cell loaded gel transplant group after incubating for 1, 3 and 7 days were added to the microcentrifuge tube and the final volume was set to be 100 µl. 1.0 ml of glycosaminoglycan Dye Reagent was added to every tube and the tubes were mixed for 30 minutes using vortex mixer. Then centrifugation was done for 10 minutes at 10,000×g. After centrifugation, supernatant was removed, tube was flipped over to remove solution remaining on walls or bottom of the tube, and absorbent paper was used. 1 ml of Blyscan Dissociation Reagent was added to a glycosaminoglycan-dye complex pellet, and dye bound to glycosaminoglycan was dissolved by using a vortex mixer for 10 minutes. Light absorbance at 656 nm was measured by using a UV spectrometer. The final concentration of GAG was determined by using a standard curve of chondroitin-4-sulfate (refer to FIG. 14).

Example 4-2

Collagen Analysis of a Stem Cell Loaded Gel Transplanted Group with Physical Stimulus Content analysis was run for collagen secreted from a culture medium of a group with a physical stimulus in an incubator and a group without the physical stimulus categorized from a stem cell loaded gel transplanted group ($5 \times 10^5$ cells/cm$^2$) inoculated on a surface of a pig tibialis tendon. Culture media after incubating for 1, 3 and 7 days were collected and collagen content analysis was run by using a collagen assay kit. The detailed methods used are as follows. A collagen solution (0-50 µg) was used as a standard reagent and was added to a microcentrifuge tube, and the final volume was set to be 100 µl by using purified water. Culture media of the stem cell loaded gel transplant group after incubating for 1, 3 and 7 days were added to the microcentrifuge tube and the final volume was set to be 100 µl. 1.0 ml of Sircol dye reagent was added to every tube and the tubes were mixed for 30 minutes using a vortex mixer. Then centrifugation was performed for 10 minutes at 10,000×g. After centrifugation, a supernatant was removed, the tube was flipped over to remove any solution remaining on walls or the bottom of the tube, and absorbent paper was used. An alkali reagent was added to a collagen-dye complex pellet, and dye bound to collagen was dissolved by using the vortex mixer for 10 minutes. Light absorbance at 550 nm was measured by using a UV spectrometer. The final concentration of collagen was determined by using a standard curve of collagen (refer to FIG. 15).

Sequence List Free Text

SEQ ID NO: 1: cagggtgttc ctggagacct

SEQ ID NO: 2: aggagagcca tcagcacctt

SEQ ID NO: 3: gaaaatggaa aacctgggga

SEQ ID NO: 4: caccctttgg accaggactt

SEQ ID NO: 5: tacagcctgg cagacctgag

SEQ ID NO: 6: attgcttggg agcagtcctt

SEQ ID NO: 7: aagggtcatc atctctgccc

SEQ ID NO: 8: gtgatggcat ggactgtggt

---

The invention claimed is:

1. A method of manufacturing an allogeneic soft-tissue transplant having autologous stem cells transplanted therein, the method comprising:
   obtaining an allogeneic soft-tissue support from a body of a human or an animal;
   washing and sterilizing the obtained allogeneic soft-tissue support;
   removing cells involved in an immunological rejection response by treating the washed and sterilized allogeneic soft-tissue support with an enzyme solution containing a mixture of trypsin, collagenase and protease;
   forming at least one pore in the allogeneic soft-tissue support by applying a superfine fiber needle to the allogeneic soft-tissue support treated with the enzyme solution and from which the cells involved in the immunological rejection response are removed;
   injecting autologous stem cells of a recipient into the at least one pore in the allogeneic soft-tissue support before or at a time of injecting an autologous stem cell loading promoter; and
   incubating the allogeneic soft-tissue support, into which the autologous stem cells are injected, to obtain an allogeneic soft-tissue transplant having autologous stem cells transplanted therein, wherein the allogeneic soft-tissue support is incubated by providing a physical stimulus to the allogeneic soft-tissue support.

2. The method of claim 1, wherein the allogeneic soft-tissue support is a ligament or a ligament connected to a bone fragment.

3. The method of claim 1, wherein the washing and sterilizing comprises
   treating the obtained allogeneic soft-tissue support with hydrogen peroxide and applying ultrasonic waves to the obtained allogeneic soft-tissue support.

4. The method of claim 3, wherein the hydrogen peroxide has a concentration in a range from about 0.1 to about 5.0% and the ultrasonic waves have an output in a range from about 120 to 400 watt.

5. The method of claim 1, wherein the washing and sterilizing comprises
   treating the obtained allogeneic soft-tissue support with a radioprotectant and irradiating the allogeneic soft-tissue support.

6. The method of claim 5, wherein the radioprotectant is cobalt-60 ($Co^{60}$) and the irradiation is gamma ray irradiation in a range from about 12 to about 50 kilogray (kGy).

7. The method of claim 1, wherein the removing of the cells involved in immunological rejection response further comprises
   water washing the sterilized allogeneic soft-tissue support with physiological saline after being treated with the enzyme solution.

8. The method of claim 1, wherein the removing of cells involved in immunological rejection response further comprises
   an osmotic treatment with distilled water to wash the allogeneic soft-tissue support after water washing of the allogeneic soft-tissue support with the physiological saline after the treatment of the washed and sterilized allogeneic soft-tissue support with an enzyme solution.

9. The method of claim 1, wherein the forming at least one pore comprises a pore having a size in a range from about 1 to about 1,000 micrometer (μm) range.

10. The method of claim 1, wherein the physical stimulus occurs at a frequency of less than 1 Hz.

11. The method of claim 1, wherein the providing a physical stimulus comprises
   providing tensile stress to two opposite distal ends of the allogeneic soft-tissue support,
   providing torsion to the allogeneic soft-tissue support in two opposite horizontal directions with respect to a vertical axis of the allogeneic soft-tissue support, or
   providing both tensile stress two opposite distal ends of the allogeneic soft-tissue support and torsion to the allogeneic soft-tissue support in two opposite horizontal directions with respect to a vertical axis of the allogeneic soft-tissue support, at the same time.

12. The method of claim 11, wherein the providing tensile stress to two opposite distal ends of the allogeneic soft-tissue support comprises extending the two opposite distal ends of the allogeneic soft-tissue support longitudinally, wherein one distal end is extended in a range of 0 to about 10% based on a total length of the allogeneic soft-tissue support and the other distal end is extended in a range of 0 to about 10% based on a total length of the allogeneic soft-tissue support, at the same time.

13. The method of claim 11, wherein the providing torsion to the allogeneic soft-tissue support in two opposite horizontal directions along a vertical axis of the allogeneic soft-tissue support comprises rotating the two opposite distal ends of the allogeneic soft-tissue support, wherein one distal end is rotated in a range of 0 to about 45 degrees clockwise and the other distal end is rotated in a range of 0 to about 45 degrees counterclockwise, at the same time.

14. The method of claim 1, wherein the incubating is performed for less than 7 days.

15. The method of claim 1, wherein the stem cell loading promoter is a collagen gel.

* * * * *